US00PP17039P2

(12) United States Plant Patent
Danziger

(10) Patent No.: US PP17,039 P2
(45) Date of Patent: Aug. 22, 2006

(54) ***TORENIA* PLANT NAMED 'DANTOMIDMON'**

(50) Latin Name: ***Torenia* sp.**
Varietal Denomination: Dantomidmon

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/138,296

(22) Filed: May 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—Foley & Lardner LLP

(57) ABSTRACT

A new and distinct *Torenia* plant named 'Dantomidmon' characterized by having shiny green foliage, doted with plenty of delicate, funnel form, cup shaped flowers in shades of pale and deep violet-blue; vigorous, bush, cascading, rounded and compact growth habit; densely branched plant, gracefully cascading from hanging baskets; early flowering response and stays in full bloom in moderate climate; suitable for use as an annual for hanging pots outdoors under partial shade; and good weather tolerance with preferred temperature range of 15 to 25° C.

2 Drawing Sheets

Botanical designation: *Torenia* sp.
Variety denomination: 'Dantomidmon'.

BACKGROUND OF THE INVENTION

The present invention relates to a new and distinct cultivar of *Torenia* plant, of the Scrophulariaceae family, hereinafter referred to by the cultivar name 'Dantomidmon'.

The new cultivar was originated in a controlled breeding program in Moshav Mishmar Hashiva, Israel. 'Dantomidmon' was discovered and selected by the inventor, Gabriel Danziger, in April of 2002 as an induced shoot mutation on a single flowering plant of the *Torenia* cultivar designated 'Dantopur' (patented, U.S. Plant Pat. No. 13,723) in Moshav Mishmar Hashiva, Israel.

'Dantomidmon' is an induced mutant of the *Torenia* cultivar 'Dantopur'. The mutation arose by radiation, as a side shoot, stabilized by removing the cutting from the mutated sector of the treated plant.

Asexual reproduction of the new cultivar by soft tip cuttings was first performed in February of 2003 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Dantomidmon' which in combination distinguish this *Torenia* as a new and distinct cultivar:

1. Shiny green foliage, doted with plenty of delicate, funnel form, cup shaped flowers in shades of pales and deep violet-blue with a distinctive yellow spot;
2. Vigorous, bush, cascading, rounded and compact growth habit;

3. Densely branched plant, gracefully cascading from hanging baskets;
4. Early flowering response and stays in full bloom in moderate climate;
5. Suitable for use as an annual for hanging pots outdoors under partial shade; and
6. Good weather tolerance with preferred temperature range of 15 to 25° C.

Of the many commercial cultivars known to the present inventor, the most similar in comparison to the new *Torenia* cultivar 'Dantomidmon' is the parental cultivar, *Torenia* 'Dantopur' (patented) in the following characteristics described in Table 1.

TABLE 1

| Character | New Cultivar 'Dantomidmon' | Parental Cultivar 'Dantopur' (patented, PP13,723) |
|---|---|---|
| Flower color | Pale and Deep Violet-Blue | Purple and blue |
| Flower size (cm) | Length: 3.5<br>Width: 3 | Length: 3.8<br>Width: 3.5 |
| Growth habit | Bush, Cascading | Bush, Cascading |
| Flowering time | 7 weeks from planting | 6 weeks from planting |

BRIEF DESCRIPTION OF THE DRAWINGS

The accompany photographs illustrate the overall appearance of the new *Torenia* cultivar 'Dantomidmon' showing the colors as true as is reasonably possible with colored reproductions of this type. Colors in the photographs may differ slightly from the color values cited in the detailed botanical description which accurately describe the colors of 'Dantomidmon'.

The first photograph shows a side perspective view of a typical flowering plant of 'Dantomidmon' in a hanging planter at 3 months of age.

Figure 1:
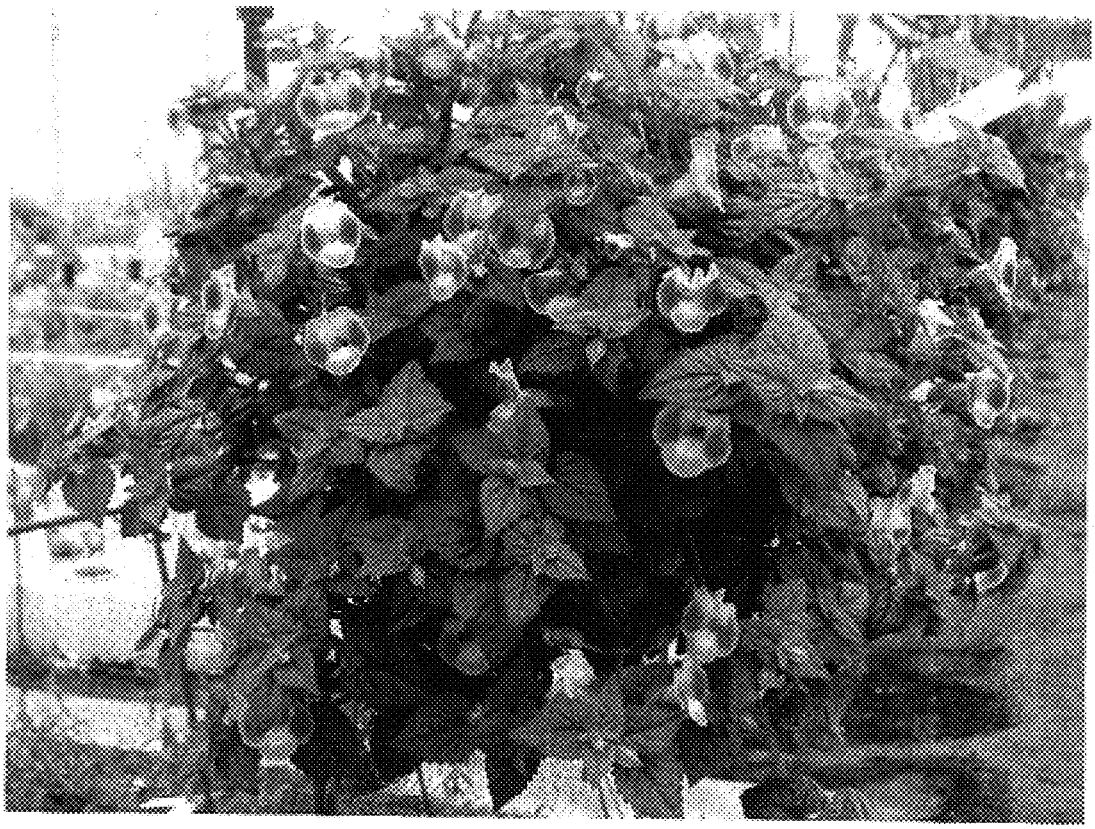
Figure 2:
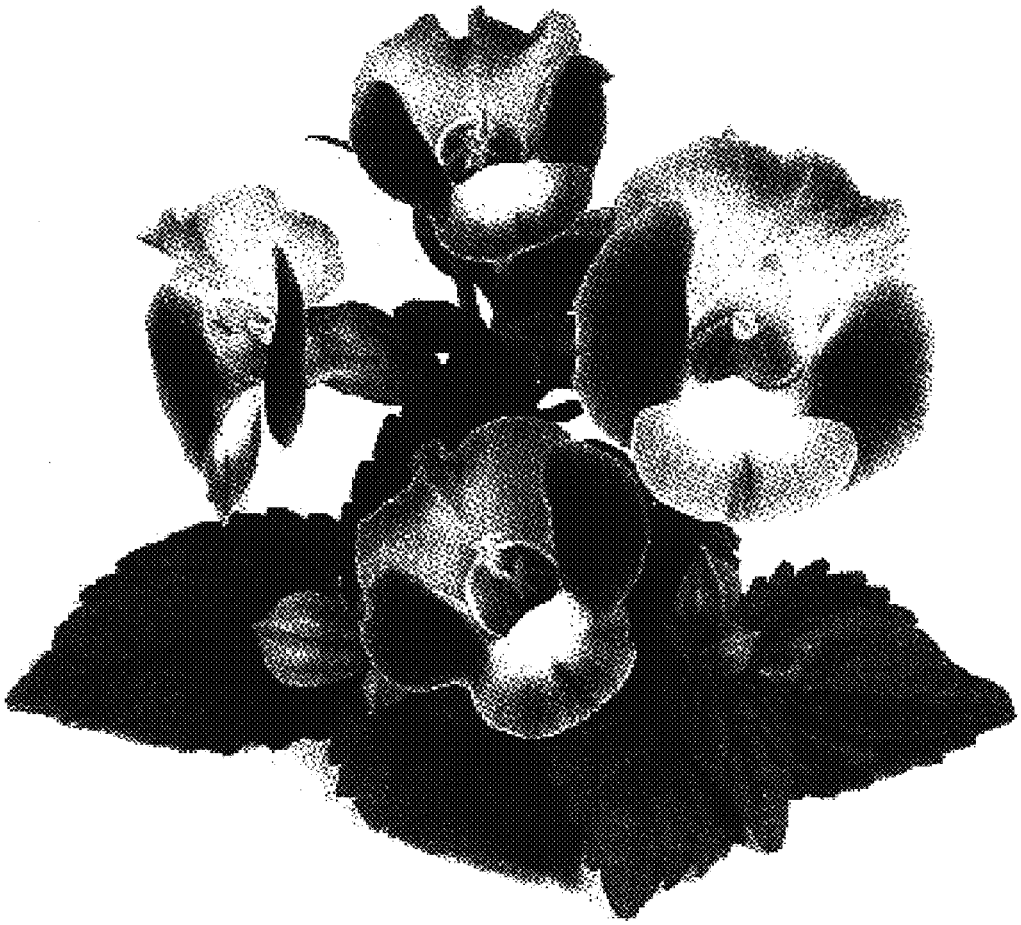

The second photograph shows a close-up view of the typical flowers, buds and leaves of 'Dantomidmon' at 3 months of age.

DETAILED BOTANICAL DESCRIPTION

The new *Torenia* cultivar 'Dantomidmon' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of the new cultivar 'Dantomidmon' as grown in a greenhouse in Moshav Mishmar Hashiva, Israel, under conditions which closely approximate those generally used in commercial practice. For use as a pot plant, plants of 'Dantomidmon' are grown outdoors in a moderate climate and grown indoors during the winter. Irrigation and fertilization are needed on a regular basis. Plants of 'Dantomidmon' are usually grown in full sunlight, but partial shade is required in mid-summer. Plants of 'Dantomidmon' are fully-grown in 3 months from planting a cutting in the summer season and bloom all year-round in a moderate climate.

Color references are made to The Royal Horticultural Society Colour Chart (R.H.S.), 2001 edition, except where general colors of ordinary significance are used. Color values were taken under daylight conditions at approximately 12:00 noon in May of 2005 in Moshav Mishmar Hashiva, Israel. The age of the plant described is 3 months.

Classification:
- *Botanical.*—*Torenia* sp.
- *Commercial.*—Midnight Moon.

Parentage:
- *Parent.*—Induced shoot mutation of *Torenia* cultivar 'Dantopur' (patented, U.S. Plant Pat. No. 13,723).

Propagation: Tissue culture (micropropagation of young in vitro plantlet) and soft tip cuttings.

Plant:
- *Form.*—Bush, cascading.
- *Growth habit.*—Vigorous, rounded and compact.
- *Height.*—15 to 20 cm.
- *Spread.*—About 50 cm.
- *Blooming period.*—All year round in moderate climate.
- *Cold tolerance.*—Frost tender. Temperature below 5° C. may damage plants.
- *Vigor.*—Plants are fully-grown in 3 months from planting a cutting in summer.

Stem:
- *Color.*—Yellow-Green, RHS 144-A.
- *Length.*—30 cm maximum length.
- *Diameter.*—About 0.3 cm.
- *Pubescence.*—Minimal and sporadic; stem is quadrangular, few hairs on the edges.
- *Branching.*—About 9 main branches grow from the base and split into hundreds of secondary branches.
- *Length of internodes.*—3.8 to 6 cm.

Foliage:
- *Overall shape.*—Deltoid.
- *Apex.*—Reniform.
- *Base.*—Cordate.
- *Size of leaf.*—Width: About 3.5 cm. Length: About 4.0 cm.
- *Margin.*—Serrate.
- *Color.*—Center color of leaf: Yellow-Green, RHS 146-A. Upper side: Yellow-Green, RHS 146-A. Under side: Yellow-Green, RHS 146-B.
- *Leaf texture: Pubescent.*

Venation:
- *Pattern.*—Mid-rib splits to 4–6 secondary veins.
- *Color.*—Upper side: Yellow-Green, RHS 146A. Under side: Yellow-Green, RHS 146A.

Petioles:
- *Length.*—About 0.6 cm.
- *Diameter.*—About 0.2 cm.
- *Color.*—Yellow-Green, RHS 146-B.

Flowers:
- *Blooming period.*—All year round in moderate climate.
- *Flowering stem.*—Flowers appear along the growing stems; about 2 to 5 flowers at end of stem.
- *Flowering longevity.*—About 4 to 7 days on the plant, dependent on temperature.
- *Type.*—Single.
- *Shape.*—Funnel form.
- *Orientation at opening.*—Slanted upward.
- *Fragrance.*—None.
- *Flower length.*—About 3.5 cm.
- *Flower width.*—About 3 cm.

Bud:
- *Shape.*—Oblong, cylindrical, ellipsoid, 5 winged.
- *Size.*—Length: About 1.5 cm. Diameter: About 0.7 cm.
- *Color.*—Yellow-green, RHS 144-A.
- *Texture.*—Pubescence on winged edges.

Floral tube:
- *Length.*—About 2.5 cm.
- *Color.*—Outside: Mixture of yellow-orange, RHS 14D, and violet-blue, RHS 92B. Inside: Mixture of yellow-orange, RHS 14A, and violet-blue, RHS 91C.

Petals:
- *Number.*—Four, fused.
- *Length.*—Upper: About 2.5 cm. Sides: About 1.8 cm. Lower: About 1.7 cm.
- *Width.*—Upper: About 1.5 cm Sides: About 1.2 cm. Lower: About 2.2 cm.
- *Shape.*—Corolla tube cylindrical or often broadened above, 2-lipped, the upper lip faintly 2-lobed, the lower lip 3-lobed.
- *Apex.*—Rounded.
- *Base.*—Fused.
- *Margin.*—Undulated.
- *Color.*—The upper lip pale violet blue, lower and sides lips deep violet blue with yellow blotch in middle lower lip. Mature: Upper side: A mixture of violet-blue shades, RHS 97C, RHS 97A, RHS 94A and RHS 94B, and yellow shade, RHS 7A. Under side: A mixture of violet-blue shades, RHS 92C and RHS 94A, and yellow shade, RHS 4D. Margin: Violet-blue, RHS 97A. Throat: Violet-blue, RHS 92B. Immature: Upper side: A mixture of violet-blue shades, RHS 97C, RHS 97A, RHS94A and RHS 94B, and yellow shade, RHS 7A. Under side: A mixture of violet-blue shades, RHS 94B and RHS 94C, with yellow shade, RHS 4D. Margin: Violet-blue, RHS 92A. Throat: Violet-blue, RHS 92B.

Sepals:
- *Number.*—5.
- *Length.*—About 1.8 cm.
- *Width.*—About 1.9 cm.
- *Shape.*—Two-lobed. 5 winged.

*Apex.*—Acute.
*Base.*—Wedge shaped.
*Margin.*—Undulated.
*Color.*—Yellow-green, RHS 144-A.

Peduncle:
*Diameter.*—About 0.25 cm.
*Length.*—1.4 to 2.5 cm.
*Texture.*—Smooth.
*Color.*—Yellow-Green, RHS 144-A.

Reproductive organs:

Androecium:
*Stamen.*—Number: 2 pairs per flower; fused. Color: White, RHS N155A.
*Anther.*—Length: About 0.4 cm. Width: About 0.05 cm. Color: White, RHS N155A.
*Spur.*—Present.
*Filament.*—Length: About 1.4 cm. Width: About 0.05 cm; lower filament shorter 0.3 cm. Color: White, RHS N155A.
*Pollen.*—Amount: Sparse amount. Color: White, RHS N155C. Requirements for pollination: Young flowers, vital pollen, and receptive, open stigma.

Gynoecium:
*Pistil.*—Number: One per flower. Length: About 2.5 cm.
*Stigma.*—Shape: Two lobes, open to opposite sides, deltoid shape. Length: About 0.25 cm. Width: About 0.3 cm. Color: White, RHS N155C.
*Style.*—Length: About 2 cm. Color: White, RHS N155C.
*Ovary.*—Number: 1. Length: About 0.5 cm. Width: About 0.2 cm. Color: Green, RHS 143-A.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'Dantomidmon', substantially as illustrated and described herein.

* * * * *